United States Patent [19]

Ishikawa et al.

[11] Patent Number: 4,652,569
[45] Date of Patent: Mar. 24, 1987

[54] THIOCYANOPYRIMIDINE, AGRICULTURAL AND HORTICULTURAL FUNGICIDE CONTAINING SAME

[75] Inventors: Katsutoshi Ishikawa, Ashigarashimo; Hitoshi Shimotori, Yokohama; Noboru Iida, Naka; Shuji Ozawa, Zushi; Shunichi Inami, Yokohama, all of Japan

[73] Assignee: Mitsui Toatsu Chemicals, Incorporated, Tokyo, Japan

[21] Appl. No.: 707,807

[22] Filed: Mar. 4, 1985

[30] Foreign Application Priority Data

Mar. 16, 1984 [JP] Japan .................................. 59-49218

[51] Int. Cl.$^4$ ................... A61K 31/505; C07D 239/02
[52] U.S. Cl. ....................................... 514/269; 71/92; 544/319
[58] Field of Search ............................ 544/319; 71/92; 514/269

[56] References Cited

FOREIGN PATENT DOCUMENTS 21939 1/1981 European Pat. Off. ............ 544/319

OTHER PUBLICATIONS

Kinugawa et al, Chem. Abst., vol. 60, 8061, 8062.
Razavi, Chem. Abst., 72-3499s.
Journal Pharmaceutical Society of Japan, vol. 83, No. 11, 1963, pp. 1086-1091.

Primary Examiner—Donald G. Daus
Assistant Examiner—C. Shen
Attorney, Agent, or Firm—Oblon, Fisher, Spivak, McClelland & Maier

[57] ABSTRACT

Disclosed herein are thiocyanopyrimidine derivatives represented by the following general formula:

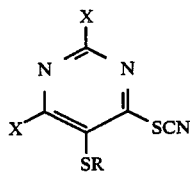

(I)

wherein R means an alkyl group having 1-3 carbon atoms and X denotes a halogen atom, their production process, and agricultural and horticultural fungicides containing same as active ingredients. The compounds of this invention can provide ideal agricultural and horticultural fungicides, since they exhibit outstanding fungicidal activities against plant pathogens led by late blight and downy mildew, their toxicity to animals are low and they are not phytotoxic.

The compounds of this invention can be obtained by reacting pyrimidine derivatives represented by the following general formula:

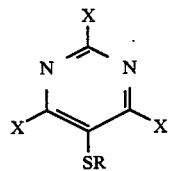

(II)

with thiocyanates while using an organic acid as a solvent. Good results can be obtained particularly when formic acid is used as a solvent.

2 Claims, No Drawings

THIOCYANOPYRIMIDINE, AGRICULTURAL AND HORTICULTURAL FUNGICIDE CONTAINING SAME

TECHNICAL FIELD

This invention relates to novel thiocyanopyrimidine derivatives, their production process, and agricultural and horticultural fungicides containing them as active ingredients.

BACKGROUND ART

The present inventors have enthusiastically studied with a principal view toward finding out those useful as agricultural and horticultural fungicides, especially toward developing fungicides capable of exhibiting activities against late blight and downy mildew which result in severe economical damages. Since the pyrimidine ring appeared to play certain special role in interaction with organism, the present inventors have studied in various ways while paying particular attention to pyrimidine derivatives.

A number of researches have hitherto been carried out on pyrimidine derivatives, resulting in the syntheses of a huge number of compounds. Many compounds have been found to have certain characteristic physiological activities in the fields of agricultural chemicals and medical drugs. However, there have still not been known any attempts of actual use of agricultural and horticultural fungicides which contain thiocyanopyrimidine derivatives each obtained by introducing a thiocyano group in the pyrimidine ring. There are very few reports dealing with the syntheses of pyrimidine derivatives containing thiocyano groups. Their biological activities are scarcely known too. They are known only to such an extent that certain thiocyanopyrimidine derivatives and their in-vitro antimicrobial activities are described in Yakugaku Zasshi, 83, 1086 (1963). In this literature, fifteen thiocyanopyrimidine derivatives and their antimicrobial activities are described. It is described that 2-(or 6-)chloro-4-methyl-6-(or 2-)thiocyanopyrimidine (hereinafter it is referred as 2-chloro-4-methyl-6-thiocyanopyrimidine) is the most active compound and the antimicrobial activities of those having substituent groups at the 5th position of the pyrimidine ring tended generally to be low. Amoung the fifteen compounds described in the above literature, it is only the above-given compound that contains a halogen atom, to say nothing of thiocyanopyrimidine derivatives containing two halogen atoms.

The present inventors carried out an investigation on thiocyanopyrimidine derivatives each of which contained two halogen atoms and in addition, an alkylthio group at the 5th position. As a result, it has surprisingly be found that these derivatives have excellent activities against numerous plant pathogens led by late blight and downy mildew and their activities can be significantly enhanced by introducing alkylthio groups to their 5th positions.

SUMMARY OF THE INVENTION

The first object of this invention is to provide novel thiocyanopyrimidine derivatives.

It is the second object of this invention to provide a production process for obtaining the above thiocyanopyrimidine derivatives.

The third object of this invention is to provide novel agricultural and horticultural fungicides which exhibit outstanding fungicidal activities against numerous plant pathogens led by late blight and downy mildew.

The above objects of this invention can be attained by providing, as a novel compound, a thiocyanopyrimidine derivative represented by the following general formula:

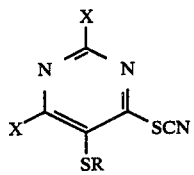

wherein R means an alkyl group having 1–3 carbon atoms and X denotes a halogen atom; a process for producing a thiocyanopyrimidine derivative represented by the following general formula:

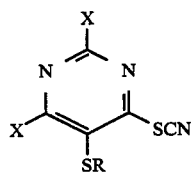

wherein R means an alkyl group having 1–3 carbon atoms and X denotes a halogen atom, which comprises reacting in an organic acid a pyrimidine derivative represented by the following general formula:

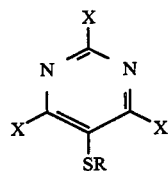

wherein R and X have the same meaning as defined above, with a thiocyanate represented by the following general formula:

MSCN (III)

wherein M means an alkali metal or ammonium; and an agricultural and horticultural fungicide comprising, as an active ingredient, a thiocyanopyrimidine derivative represented by the following general formula:

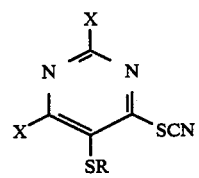

wherein R means an alkyl group having 1–3 carbon atoms and X denotes a halogen atom.

DETAILED DESCRIPTION OF THE INVENTION

Since each of the compounds of this invention contains two halogen atoms, it is possible to introduce an additional thiocyano group. However, those containing two thiocyano groups introduced therein are very inferior in activities. For example, 2,4-dichloro-5-methylthio-6-thiocyanopyrimidine which is a compound pertaining to the present invention shows strong fungicidal activities with a wide range of spectrum against plant pathogens. On the other hand, the activities of 4,6-bis(thiocyano)-2-chloro-5-methylthiopyrimidine are very inferior.

Characteristic aspects of the activities of the compounds according to this invention will be described in further detail. First of all, it can be mentioned that the types of their applicable plant diseases are numerous. For example, the compounds of this invention show, as dusts and granules or soil treatment chemicals, outstanding activities against plant diseases led by those caused by so-called Oomycetes such as potato late blight (*Phytophthora infestans*), tomato late blight (*Phytophthora infestans*), tobacco black shank (*Phytophthora parasitica var. nicotiana*), pepper phytophthora blight (*Phytophthora capsici*), cucumber downy mildew (*Pseudoperonospora cubensis*) and vine downy mildew (*Plasmopara viticola*), and including alternaria leaf spot (*Alternaria mali*), pear black spot (*Alternaria kikuchiana*), tomato early blight (*Alternaria solani*), powdery mildew, grey mold (*Botrytis cinerea*), wheat stem rust (*Puccinia qraminis*) and rice blast (*Pyricularia oryzae*). Secondly, their particularly strong activities can be mentioned. For example, they can exhibit superb fungicidal activities even when used in amounts of active ingredients far smaller than ethylenebis(zinc dithiocarbamate) which is used for the control of tomato late blight (*Phytophthora infestans*). Thirdly, it can be mentioned that they are absolutely safe to crop plants. For example, they do not show any phytotoxicity against tomato, cucumber, potato and the like. Fourthly, their extremely low toxicity to animals can also be mentioned.

The production process of each of the compounds of this invention will next be described. The compounds of this invention can each be produced in accordance with the below-described reaction scheme. Namely, in the case of a compound represented by the formula (II) in which X is either chlorine or bromine atom out of 2,4,6-trihalogenopyrimidine derivatives represented by the formula (II) or (II'), the compound may be readily produced by causing phosphorus oxychloride or phosphorus oxybromide to react with a barbituric acid derivative represented by the formula (IV) in the presence of N,N-dimethylaniline. Where R stands for a methyl group, the compounds may also be produced from the ylide compound represented by the formula (V) in accordance with the process described in Chemical Abstracts, 72, 3499s.

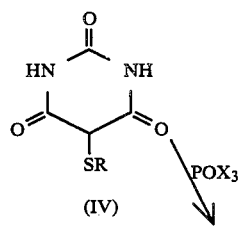
(IV)

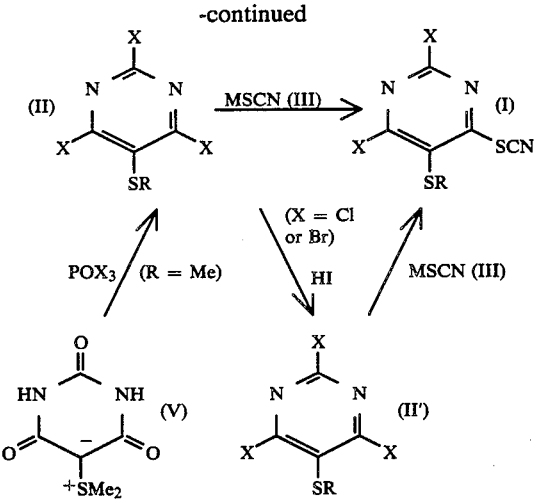

In the case of the compound represented by the formula (II') in which X denotes a iodine atom, it may be readily derived by causing conc. hydroiodic acid to react with the compound represented by the formula (II) in which X means a chlorine atom (hereinafter, the compounds of the formula (II) and formula (II') will generally be called "trihalogeno derivatives").

Description will now be made in detail on the production process of the 2,4-dihalogeno-6-thiocyanopyrimidine derivative represented by the formula (I) and pertaining to the present invention. This reaction comprises reacting the trihalogeno derivative (the compound of the formula (II) or (II')) and the thiocyanate represented by the formula (III) in a solvent. Illustrative of the thiocyanate may include potassium thiocyanate, sodium thiocyanate, ammonium thiocyanate, etc. Good results may be obtained whichever thiocyanate is employed. It is the type of solvent that affects significantly on this reaction. If reacted in an alcohol such as methanol or ethanol, the progress of the reaction will be slow even under reflux. Moreover, resinous byproducts will also be produced and the yield will be very low. If reacted in an aprotic polar solvent such as acetone, dimethyl sulfoxide, N,N-dimethylformamide or 1,3-dimethyl-2-imidazolidinone, there will be obtained those containing two or more thiocyano groups substituted therein or those converted to isothiocyanate due to rearrangement of the thiocyano group. Thus, the yield of the intended compound of the formula (I) will be low. It has however been surprisingly found that unlike these solvents, the yield can be leapingly improved when reacted in an organic acid such as formic acid, acetic acid or propionic acid. By the way, small amounts of 4,6-bis(thiocyano) derivatives may occur as byproducts depending on the type of an organic acid to be used as a solvent. These derivatives have low solubility in a recrystallization solvent to be used for the purification of the corresponding intended products of the formula (I). For the removal of such byproducts, it is necessary to repeat recrystallization several times or to separate them by column chromatography. It is however feasible to minimize the occurrence of the byproducts, 4,6-bis-(thiocyano) derivatives to trace levels or so when the reactions are carried out using formic acid as a solvent out of such organic acids. Therefore, formic acid is the best organic acid among reaction solvents useful in the practice of the production process of this invention. Although the reaction temperature may range from 10° C. to the boiling point of the solvent, it is desirable to conduct the reaction at a temperature in the range of 20°-60° C. from the viewpoints of suppression of occurrence of byproducts and suitable reaction time. The reaction time is dependent on the reaction temperature. Roughly speaking, the range of 0.5-10 hours is suitable. By the way, the reaction proceeds in a particularly short period of time when formic acid is used as a reaction solvent. Formic acid is thus the best solvent also for this reason.

After completion of the reaction, a solid is allowed to precipitate instantaneously if the resulting liquid reaction mixture is poured into a great deal of water. By collecting and drying the solid, crude crystals of the intended product (I) can be obtained with a yield of 90% or higher. Although the crude crystals have a relatively good purity as they are, a purified product may be obtained by recrystallizing them from a usual solvent such as benzene, toluene, isopropyl ether, chloroform, carbon tetrachloride, ethyl acetate, ethanol or methanol if necessary.

The above reaction can be represented by the following chemical equation, on which it will hereinafter be described in further detail.

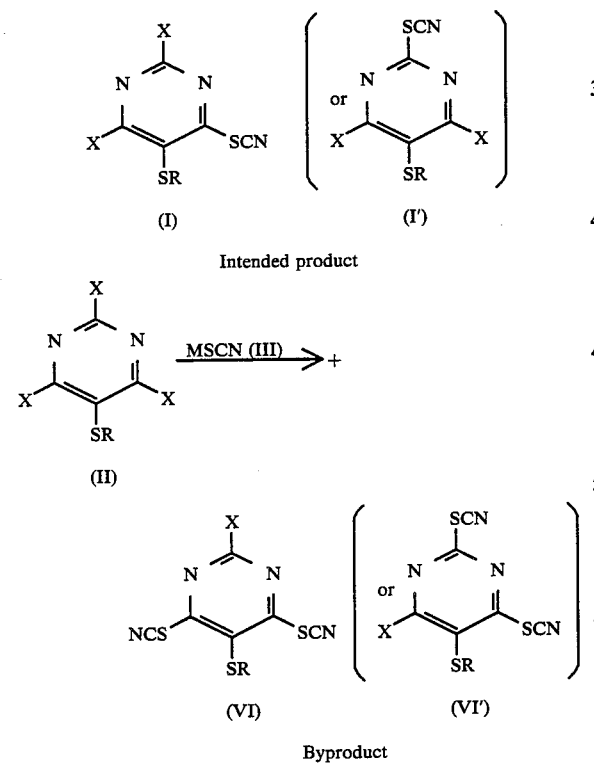

There is a chance that the compound of the formula (I) or (I') and as a byproduct, the compound of the formula (VI) or (VI') would occur if one mole of the thiocyanate is reacted with the trihalogeno derivative in the above reaction. Although it was a very difficult work to determine their structures, the present inventors have determined by means of $^{13}$C-NMR that when the thiocyanate is reacted with 5-methylthio-2,4,6-trichloropyrimidine (in the formula (II), R=Me, X=Cl), the structures of the intended compound and the byproduct are respectively represented by the formulae (I) and (VI). Namely, six signals were detected in a $^{13}$C-NMR spectrum of the intended product. The areas of these six signals were of the same intensity. Since all the carbons are not considered to be equivalent, it has been found that the intended compound has the structure of the formula (I). If it had the structure of the formula (I'), five signals should be detected with one of said signals having an intensity twice the rest. On the other hand, five signals were detected by $^{13}$C-NMR of the byproduct, of which two signals had intensities twice the remainder. Since two sets of equivalent carbons were contained, the byproduct were found to have the structure of the formula (VI).

The production process of the compound of this invention will hereinafter be described specifically by the following Synthesis Examples:

SYNTHESIS EXAMPLE 1

Synthesis of 2,4-Dichloro-5-Methylthio-6-Thiocyanopyrimidine (Compound No. 1)

In a 50-ml four-necked flask equipped with a thermometer, reflux condenser and stirrer, were charged 2.30 g (0.010 mole) of 5-methylthio-2,4,6-trichloropyrimidine and 15 ml of formic acid. While stirring the contents at room temperature, 1.07 g (0.011 mole) of potassium thiocyanate was added. Then, the resulting mixture was heated and was then stirred at 50° C. for 1 hour. After cooling the reaction mixture, it was poured into a great deal of water. The precipitated solid was collected by filtration and dried to obtain 2.34 g of crude crystals (yield: 92.9%). A portion of the crude crystals was recrystallized from ethyl acetate, thereby obtaining a purified product. m.p. 143°-144.5° C.

Elementary Analysis (as C$_6$H$_3$Cl$_2$N$_3$S$_2$):

|  | C | H | Cl | N | S |
|---|---|---|---|---|---|
| Calculated (%) | 28.58 | 1.20 | 28.12 | 16.67 | 25.43 |
| Found (%) | 28.83 | 1.04 | 28.35 | 16.63 | 25.22 |

IR (KBr): 2160 cm$^{-1}$ (—S—C≡N).

$^{13}$C—NMR $\delta^{CDCl_3}_{TMS}$ (ppm):

17.7 (C-1), 105.5 (C-2),
125.7 (C-5), 159.8 (C-3),
166.0 (C-4), 171.3 (C-6).

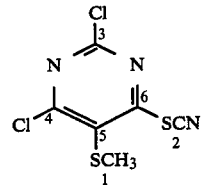

Table 1 shows compounds synthesized in a similar manner and their physical data.

TABLE 1

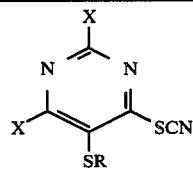

| Comp'd No. | Substituent R | Substituent X | m.p. or $^1$H—NMR | Elementary analysis data (%) (Found/Calculated) | C | H | N | Cl | S | I | Br |
|---|---|---|---|---|---|---|---|---|---|---|---|
| 2 | Et | Cl | m.p. 74–77° C. | (C$_7$H$_5$N$_3$Cl$_2$S$_2$: | 31.75 | 1.66 | 15.81 | 26.54 | 24.03 | | |
| | | | | | 31.59 | 1.89 | 15.79 | 26.64 | 24.09) | | |
| 3 | i-Pr | Cl | m.p. 63–65° C. | (C$_8$H$_7$N$_3$Cl$_2$S$_2$: | 34.56 | 2.44 | 15.01 | 25.19 | 23.14 | | |
| | | | | | 34.29 | 2.54 | 14.99 | 25.31 | 22.88) | | |
| 4 | Me | I | m.p. 155–158° C. | (C$_6$H$_3$N$_3$I$_2$S$_2$: | 16.55 | 0.67 | 9.98 | — | 15.04 | 58.06 | |
| | | | | | 16.57 | 0.70 | 9.66 | — | 14.74 | 58.34) | |
| 5 | Me | Br | $\delta^{CDCl_3}_{TMS}$ (ppm) 2.60 (s) | (C$_6$H$_3$N$_3$Br$_2$S$_2$: | 21.13 | 0.89 | 12.32 | — | 18.80 | | 46.86 |
| | | | | | 21.29 | 1.02 | 12.28 | — | 18.75 | | 46.74 |

Although the compounds according to this invention may be used as agricultural and horticultural fungicides without any additives thereto, they are actually mixed with a carrier and, if necessary, other adjuvants and processed for their application into preparation forms commonly employed as agricultural and horticultural fungicides and containing their active ingredients within the range of 0.01–90 wt. %, for example, dust (concentrations of active ingredients: 1–10 wt. %), coarse dust (concentrations of active ingredients: 1–10 wt. %), micro-granules (concentrations of active ingredients: 1–25 wt. %), granules (concentrations of active ingredients: 2–30 wt. %), wettable powder (concentrations of active ingredients: 20–80 wt. %), oil suspension (concentrations of active ingredients: 10–70 wt. %), smoking agents (concentrations of active ingredients: 2–70 wt. %), microcapsules (concentrations of active ingredients: 10–80 wt. %), flowable formulations (concentrations of active ingredients: 20–60 wt. %) and the like.

By the term "carrier" as used herein is meant a synthetic or natural, inorganic or organic substance which is incorporated in agricultural and horticultural fungicides to assist their active ingredients to reach locations to be treated therewith and to facilitate the storage, transportation and handling of such active ingredients.

As solid carriers suitable for use in the practice of this invention, may be mentioned clays such as montmorillonite and kaolinite, inorganic materials such as diatomaceous earth, terra alba, talc, vermiculite, gypsum, calcium carbonate, silica gel, ammonium sulfate and the like, vegetable- or plant-origin organic materials such as soybean flour, saw dust, wheat flour and the like, urea, etc.

Among suitable liquid carriers, may be included aromatic hydrocarbons such as benzene, toluene, xylene, cumene, etc., paraffinic hydrocarbons such as kerosine, mineral oil and the like, halogenated hydrocarbons such as carbon tetrachloride, chloroform, dichloroethane and the like, ketones such as acetone, methyl ethyl ketone, etc., ethers such as dioxane, tetrahydrofuran and the like, alcohols such as methanol, propanol, ethylene glycol and the like, dimethyl formamide, dimethylsulfoxide, water, etc.

In order to enhance the effectiveness of the compound according to this invention, it is possible to use such adjuvants as given below either singly or in combination in accordance with the purpose of each application thereof while taking into consideration the types of their preparation forms and their application fields.

Namely, exemplary adjuvants may include anionic surfactants such as alkyl sulfates, aryl sulfonates, succinates, polyethylene glycol alkyl aryl ether sulfates, and the like, cationic surfactants such as alkylamines, polyoxyethylene alkylamines, etc., non-ionic surfactants such as polyoxyethylene glycol ethers, polyoxyethylene glycol esters, polyol esters and the like, and amphoteric surfactants.

Besides, may be mentioned as stabilizers, thickeners, lubricants and the like isopropyl hydrogenphosphate, calcium stearate, wax, casein lime, sodium alginate, methylcellulose, carboxymethylcellulose, gum arabic, etc. However, it should be borne in mind that these ingredients are not limited to the above-recited examples.

The compounds of this invention, being used as fungicides, may be applied simultaneously with or as mixtures with other agricultural chemicals such as insecticides, other fungicides, acaricides, nematocides, antiviral agents, herbicides, plant growth regulators and attractants, for example, organo-phosphorous compounds, carbamate-type compounds, dithiocarbamate-type compounds, thiolcarbamate-type compounds, organochlorine compounds, dinitro compounds, antibiotics, urea-base compounds, triazine-type compounds, fertilizers, etc.

A variety of preparations or applicable compositions containing the above-described active ingredients according to this invention may be used in accordance with application methods commonly adopted in the production field of agricultural chemicals, namely, by applying them over the surfaces of fields, plants or the like (e.g., spraying them as liquid compositions, misting, atomizing, dusting, granular application, submerged application); smoking and soil application (for example, mixing, soil drench); surface application (for example, coating, dressing); dipping; and the like application methods.

The amount of application may vary depending on the type of disease and the stage of growth of crop or plant. It may however be applied in an amount of 0.2–4 kg per hectare and usually 0.5–2 kg per hectare in terms of an active ingredient.

Certain examples of preparations of agricultural and horticultural fungicides containing the compounds according to this invention as active ingredients will be described below. Needless to say, the present invention is not limited to use of the additives, their proportions, use of the active ingredients and their contents which will follow. Compounds of this invention, which will be used as active ingredients, will be expressed in terms of the compound number given in the above Table 1. All designations of "parts" will mean "parts by weight".

PREPARATION EXAMPLE 1

Wettable Powder

Wettable powder, which contained 30% of Compound No. 1 as an active ingredient, was prepare by uniformly milling and mixing 300 parts of Compound No. 1, 44o parts of diatomaceous earth, 200 parts of terra abla, 25 parts of sodium lignosulfonate, 15 parts of sodium alkylbenzenesulfonate (the carbon numbers of the alkyl groups: 10–15), and 20 parts of polyoxyethylene nonyl phenyl ether (the polymerization degree of the polyoxyethylene moiety: 5–10).

PREPARATION EXAMPLE 2

Granules

Granules, which contained 10% of Compound No 2 as an active ingredient, was prepared by mixing 10 parts of Compound No. 2, 62 parts of bentonite, 20 parts of talc, 2 parts of sodium dodecylbenzenesulfonate and 1 part of sodium lignosulfonate, kneading the resultant mixture with a suitable amount of water, and then granulating the thus-kneaded mass by an extrusion-granulating machine in a manner known per se in the art.

PREPARATION EXAMPLE 3

Dust

Dust, which contained 2% of Compound No. 2 as an active ingredient, was prepared by uniformly milling and mixing 20 parts of Compound No. 2, 5 parts of calcium stearate, 5 parts of powdery silica gel, 200 parts of diatomaceous earth, 300 parts of terra abla, and 470 parts of talc.

PREPARATION EXAMPLE 4

Coarse Dust

Coarse dust, which contained 5% of Compound No. 1 as an active ingredient, was obtained by mixing, in a V-blender, 5 parts of Compound No. 1 which had been ground in a jet mill, 94.5 parts of granular calcium carbonate (grain size: 0.1–0.25 mm) and 0.5 part of soybean oil.

PREPARATION EXAMPLE 5

Micro-Granules

Micro-granules, which contained 5% of Compound No. 3 as an active ingredient, was obtained by mixing, in a V-blender, 5 parts of Compound No. 3 which had been ground in a jet mill, 94.5 parts of granular calcium carbonate (grain size: 0.3–0.6 mm) and 0.5 parts of soybean oil.

PREPARATION EXAMPLE 6

Flowable Formulation

A flowable formulation, which contained 40% of Compound No. 4, was obtained by finely grinding, in a sand grinder, 40 parts of Compound No. 4, 15 parts of ethylene glycol, 0.1 part of Deltop® (product of Takeda Chemical Industries, Ltd. organoiodine compound), 3 parts of Demol-N® (product of Kao Corporation; special naphthalene condensate), 0.2 part of polyvinylpyrrolidone and 41.7 parts of water.

Test 1

Alternaria Leaf Spot (*Alternaria mali*) Control Test

Newly-grown branches of an apple tree (cultivar: Star King) were put in 200-ml Erlenmeyer flasks and were sprayed to the point of 50 ml per 3 branches with a chemical formulation of a predetermined concentration (each sample compound was prepared into wettable powder in accordance with the procedure of Preparation Example 1 and then diluted to the predetermined concentration with water), using a spray gun (1.0 kg/cm$^2$). After allowing the branches to dry in air, they were sprayed and inoculated with a spore suspension of *Alternaria mali* which had in advance been cultured for 7 days in a culture medium of "V-8" ® vegetable juice. The branches were then incubated for 3 days at 23°–25° C. and at a humidity of 95% or higher. The number of lesions was counted with respect to each of 7 leaves on each branch. The number of lesions per branch was then calculated with respect to 3 branches in each group, on which was determined a control value in accordance with the following equation:

$$\text{Control value} = \left(1 - \frac{\text{Number of lesions in treated group}}{\text{Number of lesions in untreated group}}\right) \times 100$$

Upon conducting the above test, the following Compounds A and B were used as controls for comparison.

Control Compound A: 2-Chloro-4-methyl-6-thiocyanopyrimidine, a compound described in Yakugaku Zasshi, 83, 1086 (1963).

Control Compound B: N-(p-Fluorophenyl)-dichloromaleimide, a compound commercially available as a control agent for alternaria leaf spot (*Alternaria mali*).

Results are shown in Table 2.

TABLE 2

| Sample comp'd No. | Concentration of active ingredient (ppm) | Control value | Phyto-toxicity |
|---|---|---|---|
| 1 | 250 | 100 | none |
| 2 | 250 | 100 | none |
| 3 | 250 | 100 | none |
| 4 | 250 | 100 | none |
| 5 | 250 | 100 | none |
| Control Comp'd A | 250 | 20 | none |
| Control Comp'd B | 250 | 58 | none |
| Untreated | — | 0 | — |

As shown in Table 2, the control compound known from literatures, 2-chloro-4-methyl-6-thiocyanopyrimidine did not show any substantial activities. It is also clear that the compounds of this invention have superior activities than N-(p-fluorophenyl)dichloromaleimide commercially available as a control agent for alternaria leaf spot (*Alternaria mali*).

Test 2

Cucumber Grey Mold (*Botrytis cinerea*) Control Test

Cucumber plants (cultivar: Sagami-Hanjiro; in the cotyledon stage), which had been cultivated individually in pots in a green house, were sprayed to the point of 20 ml per 3 pots with a chemical formulation of a predetermined concentration (prepared by converting each sample compound into wettable powder in the same manner as in Preparation Example 1 and then diluting the wettable powder with water to the predetermined concentration), using a spray gun (1.0 kg/cm$^2$), and then dried in air. From *Botrytis cinerea* which had in advance been cultured on a PDA culture medium, a spore suspension was prepared. The spore suspension was sprayed and inoculated onto the cucumber plants in the pots. The thus-inoculated cucumber plants were immediately incubated at temperatures of 22°–24° C. and humidity of 95% or higher for 5 days. The extents of development of lesions on the cotyledons were then investigated.

The following rank reading was employed:

| Lesion Index | Percent Leaf Area Infected |
|---|---|
| 0 | 0% |
| 1 | 1–10% |
| 2 | 11–25% |
| 3 | 26–50% |
| 4 | 51% and up |

Lesion indexes were determined for all the cotyledons, on which average values were calculated separately as lesion indexes for the individual groups. By the way, each group was composed of 3 pots each of which contained 5 plants.

Upon conducting the above test, the above Control Compound A and the following Control Compound C were used for comparison.

Control Compound C: Methyl 1-butylcarbamoyl-2-benzimidazol-carbamate, a compound commercially available as a control agent for grey mold (*Botrytis cinerea*).

Results are shown in Table 3.

TABLE 3

| Sample comp'd No. | Concentration of active ingredient (ppm) | Lesion index | Phytotoxicity |
|---|---|---|---|
| 1 | 250 | 0 | none |
| 2 | 250 | 0 | none |
| 3 | 250 | 0 | none |
| 4 | 250 | 0 | none |
| 5 | 250 | 0 | none |
| Control Comp'd A | 250 | 3.5 | none |
| Control Comp'd C | 250 | 3.0 | none |
| Untreated | — | 3.5 | — |

As apparent from Table 3, the control compound known from literatures, 2-chloro-4-methyl-6-thiocyanopyrimidine did not show any substantial activities. Similarly, methyl 1-butylcarbamoyl-2-benzimidazolcarbamate which was available commercially as a control agent for grey mold (*Botrytis cinerea*) did not show any substantial activities in the present test. It is thus clear that the compounds of this invention have superior activities.

Test 3

Tomato Late Blight (*Phytophthora infestans*) Control Test

Tomato plants (cultivar: Sekaiichi; about 25 cm in hight), which had been cultivated in pots in a green house, were sprayed to the point of 50 ml per 3 pots with a chemical formulation of a predetermined concentration (each sample compound was prepared into wettable powder in accordance with the procedure of Preparation Example 1 and then diluted with water to the predetermined concentration), using a spray gun. The plants were then dried in air. A zoospore suspension was prepared from *Phytophthora infestans* which had in advance been cultured for 7 days on potato pieces. The tomato plants, which had been sprayed with the chemical formulation, were sprayed and inoculated with the zoospore suspension. The sample plants were incubated for 6 days at temperatures of 17°–19° C. and humidity of 95% or higher. Thereafter, the extent of lesion development was investigated.

The following rank reading was employed:

| Lesion Index | Percent Leaf Area Infected |
|---|---|
| 0 | 0% |
| 1 | 1–5% |
| 2 | 6–25% |
| 3 | 26–50% |
| 4 | 51% and up |

Lesion indexes were determined for all the leaves except for newly-developed two leaves in the above-described manner, on which average values were calculated separately as lesion indexes for the individual groups.

Upon conducting the above test, the above Control Compound A and the following Control Compound D were used for comparison.

Control Compound D: Zinc ethylenebis(dithiocarbamate), a compound commercially available as a control agent for tomato late blight (*Phytophthora infestans*) and potato late blight (*Phytophthora infestans*).

Results are shown in Table 4.

TABLE 4

| Sample comp'd No. | Concentration of active ingredient (ppm) | Lesion index | Phytotoxicity |
|---|---|---|---|
| 1 | 200 | 0 | none |
| 2 | 200 | 0 | none |
| 3 | 200 | 0 | none |
| 4 | 200 | 0 | none |
| 5 | 200 | 0 | none |
| Control Comp'd A | 200 | 3.9 | none |
| Control Comp'd D | 200 | 2.0 | none |
| Untreated | — | 4.0 | — |

As shown in Table 4, the control compound known from literatures, 2-chloro-4-methyl-6-thiocyanopyrimidine did not show any substantial activities. It is also clear that the compounds of this invention have superior activities than zinc ethylenebis(dithiocarbamate) commercially available as a control agent for late blight.

Test 4

Potato Late Blight (*Phytophthora infestans*) Control Test

Potato plants (cultivar: Danshaku; about 25 cm tall), which had been individually cultivated in pots in a green house, were sprayed to the point of 50 ml per 3 pots with a chemical formulation of a predetermined concentration (each sample compound was prepared into wettable powder in accordance with the procedure of Preparation Example 1 and then diluted with water to the predetermined concentration), using a spray gun (1.0 kg/cm²). The plants were then dried in air. A zoospore suspension was prepared from *Phytophthora infestans* which had in advance been cultured for 7 days on potato pieces. The potato plants, which had been sprayed with the chemical formulation, were sprayed and inoculated with the zoospore suspension. The sample plants were incubated for 6 days at temperatures of 17°-19° C. and humidity of 95% or higher. Thereafter, the extent of lesion development was investigated.

The rank reading and the calculation method of lesion indexes, both described in Test 3, were followed.

Upon conducting the above test, the above-described Control Compounds A and D were used.

Results are shown in Table 5.

TABLE 5

| Sample comp'd No. | Concentration of active ingredient (ppm) | Lesion index | Phytotoxicity |
| --- | --- | --- | --- |
| 1 | 200 | 0 | none |
| 2 | 200 | 0 | none |
| 3 | 200 | 0 | none |
| 4 | 200 | 0 | none |
| 5 | 200 | 0 | none |
| Control Comp'd A | 200 | 3.5 | none |
| Control Comp'd D | 200 | 2.6 | none |
| Untreated | — | 4.0 | — |

As apparent from Table 5, the control compound known from literatures, 2-chloro-4-methyl-6-thiocyanopyrimidine did not show any substantial activities. It is also clear that the compounds of this invention have superior activities than zinc ethylenebis(dithiocarbamate) commercially available as a control agent for late blight.

Test 5

Cucumber Downy Mildew (*Pseudoperonospora cubensis*) Control Test

Cucumber plants (cultivar: Sagami-Hanjiro; in the two leaf stage), which had been cultivated individually in pots in a green house, were sprayed to the point of 30 ml per 3 pots with a chemical formulation of a predetermined concentration (prepared by converting each sample compound into wettable powder in the same manner as in Preparation Example 1 and then diluting the wettable powder with water to the predetermined concentration), using a spray gun (1.0 kg/cm²), and then dried in air. Spore of *Pseudoperonospora cubensis* was collected from infected areas of cucumber leaves which had been infected by downy mildew. Using the thus-collected spore of *Pseudoperonospora cubensis* and deionized water, a spore suspension was prepared. The spore suspension was sprayed and inoculated onto the cucumber plants in the pots. The thus-inoculated cucumber plants were immediately incubated at temperatures of 17°-19° C. and humidity of 95% or higher for 24 hours and then transferred into a green house (temperature: 18°-2720 C.). After an elapsed time of 7 days, the extent of development of lesions was investigated. The same rank reading as that used in Test 3 was also used.

Upon conducting the above test, the above Control Compound A and the following Control Compound E were used for comparison.

Control Compound E: N-(trichloromethylthio)-4-cyclohexene-1,2-dicarboximide, a compound commercially available as a control agent for cucumber downy mildew (*Pseudoperonospora cubensis*).

Results are shown in Table 6.

TABLE 6

| Sample comp'd No. | Concentration of active ingredient (ppm) | Lesion index | Phytotoxicity |
| --- | --- | --- | --- |
| 1 | 200 | 0 | none |
| 2 | 200 | 0 | none |
| 3 | 200 | 0 | none |
| 4 | 200 | 0 | none |
| 5 | 200 | 0 | none |
| Control Comp'd A | 200 | 3.2 | none |
| Control Comp'd E | 200 | 2.4 | none |
| Untreated | — | 3.7 | — |

As apparent from Table 6, the control compound known from literatures, 2-chloro-4-methyl-6-thiocyanopyrimidine did not show any substantial activities. Similarly, N-(trichloromethylthio)-4-cyclohexene-1,2-dicarboximide did not exibit much activities. It is thus understood that the compounds of this invention have superior activities.

Test 6

Cucumber Powdery Mildew (*sphaerotheca fuliginea*) Control Test

Cucumber plants (cultivar: Sagami-Hanjiro; in the two leaf stage), which had been cultivated individually in pots in a green house, were sprayed to the point of 30 ml per 3 pots with a chemical formulation of a predetermined concentration (prepared by converting each sample compound into wettable powder in the same manner as in Preparation Example 1 and then diluting the wettable powder with water to the predetermined concentration), using a spray gun (1.0 kg/cm²), and then dried in air. Spore of *Sphaerotheca fuliginea* was collected from infected areas of cucumber leaves which had been infected by powdery mildew. Using the thus-collected spore of *Sphaerotheca fuliginea* and deionized water, a spore suspension was prepared. The spore suspension was sprayed and inoculated onto the cucumber plants in the pots. The thus-inoculated cucumber plants were placed in a green house (temperature: 18°-27° C.). Eight days later, the extent of development of lesions was investigated. The rank reading was the same as that employed above (in Test 3).

Upon conducting the above test, the above Control Compound A and the following Control Compound F were used for comparison.

Control Compound F: Dimethyl 4,4'-o-phenylenebis(3-thioallophanate), a chemical commercially available as a control agent for cucumber powdery mildew (*Sphaerotheca fuliginea*).

Results are shown in Table 7.

TABLE 7

| Sample comp'd No. | Concentration of active ingredient (ppm) | Lesion index | Phytotoxicity |
| --- | --- | --- | --- |
| 1 | 250 | 0 | none |
| 2 | 250 | 0.2 | none |
| 3 | 250 | 0.3 | none |
| 4 | 250 | 0.1 | none |
| 5 | 250 | 0.1 | none |
| Control Comp'd A | 250 | 2.4 | none |
| Control | 250 | 0.9 | none |

TABLE 7-continued

| Sample comp'd No. | Concentration of active ingredient (ppm) | Lesion index | Phyto-toxicity |
|---|---|---|---|
| Comp'd F | | | |
| Untreated | — | 4.0 | — |

Test 7

Rice Blast (*Pyricularia Oryzae*) Control Test

Paddy-rice seedlings (cultivar: Sasanishiki; in the 5–6 leaf stage), which had been allowed to grow in pots in a green house, were sprayed to the point of 30 ml per 3 pots with a chemical formulation of a predetermined concentration (prepared by converting each sample compound into wettable powder in the same manner as in Preparation Example 1 and then diluting the wettable powder with water to the predetermined concentration), using a spray gun (1.0 kg/cm$^2$), and then dried in air. *Pyricularia oryzae*, which had in advance been cultured on a culture medium making use of rice straws, was sprayed and inoculated onto the thus-treated paddy-rice seedlings in a wet room having humidity of 90% or higher (temperature: 24°–28° C.). After holding then in the wet room for 7 days, the extent of development of lesions was investigated.

The following rank reading was employed:

| Lesion Index | Number of Lesions |
|---|---|
| 0 | No lesion |
| 1 | 1–2/leaf |
| 2 | 3–5/leaf |
| 3 | 6–10/leaf |
| 4 | 11 and up |

Ten leaves were chosen at random per each pot. The lesion index was determined in the above manner for each of the leaves. An average value was then calculated as a lesion index for each test group.

Upon conducting the above test, the above Control Compound A and the following Control Compound G were used for comparison.

Control Compound G: O-Ethyl-S,S-diphenyl dithiophosphate, a chemical available commercially as a control for rice blast (*pyricularia oryzae*).

Results are shown in Table 8.

TABLE 8

| Sample comp'd No. | Concentration of active ingredient (ppm) | Lesion index | Phyto-toxicity |
|---|---|---|---|
| 1 | 250 | 0 | none |
| 2 | 250 | 0 | none |
| 3 | 250 | 0.2 | none |
| 4 | 250 | 0.2 | none |
| 5 | 250 | 0.2 | none |
| Control Comp'd A | 250 | 2.6 | none |
| Control Comp'd G | 250 | 0 | none |
| Untreated | — | 3.5 | — |

Test 8

Vine Downy Mildew (*Plasmopara viticola*) Control Test

Young vine plants (Cultivar: Neomuscat: 2 year-old plant), which had been cultivated in pots, were sprayed to the point of 100 ml per 2 pots with a chemical formulation of a predetermined concentration (prepared by converting each sample compound into wettable powder in the same manner as in Preparation Example 1 and then diluting the wettable powder with water to the predetermined concentration), using a spray gun (1.0 kg/cm$^2$), and then dried in air. *Plasmopara viticola* was collected from infected areas of vine leaves which had been infected by downy mildew. Using the thus-collected *Plasmopara viticola* and deionized water, a spore suspension was prepared. The spore suspension was sprayed and inoculated onto the vine plants. After holding the thus-inoculated vine plants for 24 hours in a wet room (humidity: 90% or higher; temperature: 18°–20° C.), they were transferred to a green house (temperature: 18°–25° C. to accelerate development of the disease. The extent of lesion development was investigated ten days later. The rank reading was the same as that employed in Test 3.

Upon conducting the above test, the above Control Compounds A and D were used for comparison.

Results are shown in Table 9.

TABLE 9

| Sample comp'd No. | Concentration of active ingredient (ppm) | Lesion index | Phyto-toxicity |
|---|---|---|---|
| 1 | 250 | 0 | none |
| 2 | 250 | 0.2 | none |
| 3 | 250 | 0 | none |
| 4 | 250 | 0 | none |
| 5 | 250 | 0 | none |
| Control Comp'd A | 250 | 3.2 | none |
| Control Comp'd D | 250 | 0.8 | none |
| Untreated | — | 3.8 | — |

We claim:

1. A thiocyanopyrimidine represented by the following formula;

(I)

wherein R means an alkyl group having 1–3 carbon atoms and X denotes a halogen atom.

2. An agricultural and horticultural fungicide comprising, as an active ingredient, a thiocyanopyrimidine represented by the following general:

(I)

wherein R means an alkyl group having 1–3 carbon atoms and X denotes a halogen atom.

* * * * *